United States Patent
Zijlstra et al.

(10) Patent No.: US 11,864,790 B2
(45) Date of Patent: Jan. 9, 2024

(54) VASCOSCOPE

(71) Applicant: UMC UTRECHT HOLDING B.V., Utrecht (NL)

(72) Inventors: Jan Zijlstra, Utrecht (NL); Huibert Alexander Tjabbes, Utrecht (NL); Marlies Van Dullemen, Utrecht (NL); Leon Vincent Neve, Utrecht (NL); Fransiscus Petrus Cornelis Goethals, Utrecht (NL); Jesse Mattan Bosma, Utrecht (NL); Jeroen Van Den Berg, Putten (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 241 days.

(21) Appl. No.: 17/280,749

(22) PCT Filed: Sep. 26, 2019

(86) PCT No.: PCT/NL2019/050648
§ 371 (c)(1),
(2) Date: Mar. 26, 2021

(87) PCT Pub. No.: WO2020/067897
PCT Pub. Date: Apr. 2, 2020

(65) Prior Publication Data
US 2022/0039829 A1    Feb. 10, 2022

(30) Foreign Application Priority Data

Sep. 27, 2018  (NL) .................................. 2021720
Apr. 23, 2019  (NL) .................................. 2022996

(51) Int. Cl.
| A61B 17/34 | (2006.01) |
| A61B 8/08  | (2006.01) |
| A61B 8/00  | (2006.01) |

(52) U.S. Cl.
CPC .......... *A61B 17/3403* (2013.01); *A61B 8/085* (2013.01); *A61B 8/4411* (2013.01);
(Continued)

(58) Field of Classification Search
CPC ... A61B 17/3403; A61B 8/085; A61B 8/4411; A61B 8/4455; A61B 8/4472;
(Continued)

(56) References Cited

U.S. PATENT DOCUMENTS 5,167,630 A     12/1992  Paul
6,139,496 A *   10/2000  Chen .................... A61B 8/4444
                                                       600/459
(Continued)

FOREIGN PATENT DOCUMENTS

| EP | 2078495 A1   | 7/2009 |
| EP | 2666414 A1   | 11/2013 |
| WO | 2010111525 A9 | 4/2011 |

*Primary Examiner* — Boniface Ngathi
*Assistant Examiner* — Zainab Mohammed Aldarraji
(74) *Attorney, Agent, or Firm* — AEON Law, PLLC; Adam L. K. Philipp; David Cohen

(57) ABSTRACT

The present invention is in the field of an improved device for assisting entry of a needle into a vein or a shunt using ultra-sound, also referred to as a vascoscope, a kit of parts comprising said vascoscope, and a method of entering a needle in a vein or shunt, comprising use of said vascoscope. The present vascoscope is especially suited for use in dialysis and is aimed at preventing damage such as in repetitive use applications.

19 Claims, 7 Drawing Sheets

(52) U.S. Cl.
CPC .......... *A61B 8/4455* (2013.01); *A61B 8/4472* (2013.01); *A61B 8/4494* (2013.01); *A61B 8/462* (2013.01); *A61B 8/467* (2013.01); *A61B 8/54* (2013.01); *A61B 8/4227* (2013.01); *A61B 2017/3413* (2013.01)

(58) Field of Classification Search
CPC ....... A61B 8/4494; A61B 8/462; A61B 8/467; A61B 8/54; A61B 8/4227; A61B 2017/3413; A61B 8/0841; A61B 8/476
See application file for complete search history.

(56) References Cited

U.S. PATENT DOCUMENTS

| | | | |
|---|---|---|---|
| 11,474,219 B2* | 10/2022 | Otsuka | A61B 8/546 |
| 2007/0016030 A1* | 1/2007 | Stringer | G01S 7/5208 |
| | | | 600/437 |
| 2013/0131501 A1 | 5/2013 | Blaivas et al. | |
| 2017/0042507 A1* | 2/2017 | Koning | A61B 8/4494 |
| 2018/0263597 A1* | 9/2018 | Tchang | G10K 11/355 |
| 2019/0162832 A1* | 5/2019 | Otsuka | G01S 7/52079 |
| 2022/0389192 A1* | 12/2022 | Kawaji | C08K 7/00 |

\* cited by examiner

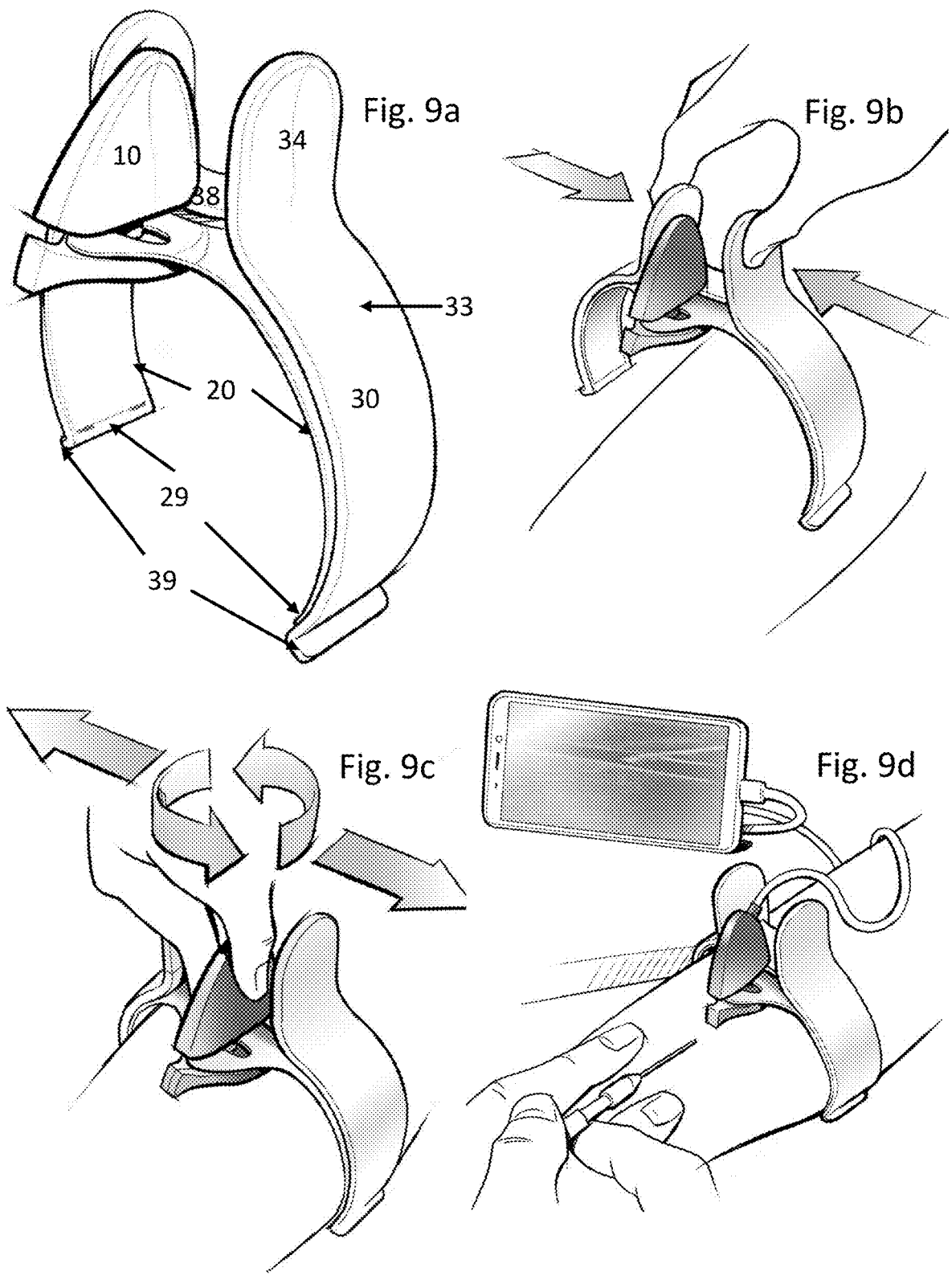

VASCOSCOPE

RELATED APPLICATIONS

This application is a U.S. National Phase of PCT Patent Application No. PCT/NL2019/050648 having International filing date of Sep. 26, 2019, which claims the benefit of priority of a Netherlands Patent Application No. NL2021720, filed Sep. 27, 2018, and a Netherlands Patent Application No. NL2022996, filed Apr. 23, 2019. The entire contents of the above-referenced applications and of all priority documents referenced in the Application Data Sheet filed herewith are hereby incorporated by reference for all purposes.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

FIELD OF THE INVENTION

The present invention is in the field of an improved device for assisting entry of a needle into a vein or a shunt using ultrasound, also referred to as a vascoscope, a kit of parts comprising said vascoscope, and a method of entering a needle in a vein or shunt, comprising use of said vascoscope. The present vascoscope is especially suited for use in dialysis and is aimed at preventing damage such as in repetitive use applications.

BACKGROUND OF THE INVENTION

Patients with severe kidney disease and in need of haemodialysis (HD) require a so-called shunt to receive treatment. A shunt may be created by making an artificial connection between an artery and a vein, most often in the lower arm. In the Netherlands, 5,500 kidney patients receive HD three times a week, which means each patient's shunt needs to be accessed about 300 times per year (divided over two needles. An urgent and common problem is the difficulty of accessing the shunt properly. In 20-40% of the cases the shunt is missed or the needle is pierced through the back wall of the shunt. This so-called mis-cannulation is painful for the patient and can lead to an internal bleeding, an infection, scarring, and to narrowing and blockage of the shunt. In addition, it typically becomes increasingly difficult to puncture successfully a next time. Multiple miscannulations result in a shorter shunt lifetime, and as a consequence a new shunt needs to be placed, which is a costly and requires an invasive procedure.

Research on miscannulation shows these risks could be reduced to 10% if ultrasound is used to guide puncturing of the shunt. Therefore the shunt survives substantially longer leading to a yearly cost reduction of € 1,796 per patient.

In dialysis centres in the Netherlands less than 10% of the punctures are under ultrasound-guidance. However, the current equipment available for dialysis staff encounters several problems. First, the equipment is too complex to operate because it is considered to contain unnecessary features and is too comprehensive and rather complex to handle. Second, the current equipment is in fact not designed to support this specific procedure; when applying ultrasound guidance one hand is used to hold the probe in the right position, while the other hand directs the needle. A frequently cited reason for not using ultrasound equipment is that caretakers indicate that they need an extra third hand for the procedure. Additionally, holding the probe requires attention which distracts from the cannulation process. The dialysis staff may receive training to gain experience on this multifunctional process, but for the majority it remains a too complex task.

In a more general sense it is widely accepted that central venous cannulation is best done under ultrasound guidance (Hind et al, 2003). Guidelines for central venous access also recommend to use ultrasound: Guidelines EDTA (guideline 10) (Vascular Access Society; website) and Practice Guidelines for Central Venous Access (American Society of Anaesthesiologists; Anaesthesiology 2012). The AIUM (American Institute of Ultrasound in Medicine) advises a two-person procedure to overcome the third hand issue, but this is seldom in daily practice. Single nurse approaches are most common, such as relying on imaging while skipping tactile feedback, holding an ultrasound probe while performing an acrobatic two finger tactile feedback on the shunt or using ultrasound not as guidance but for preparation and post procedure check only. Despite this motivation ultrasound guidance is not widely used yet for central venous access.

Ultrasound is an oscillating sound pressure wave with a frequency greater than the upper limit of the human hearing range (hence ultra-sound). Ultrasound devices may operate with frequencies from 20 kHz up to several gigahertz. Ultrasound may be used in many different fields. Ultrasonic devices are used to detect objects and measure distances. Ultrasonic imaging (sonography) is used in both veterinary medicine and human medicine. In the non-destructive testing of products and structures, ultrasound is used to detect invisible flaws. Industrially, ultrasound is used for cleaning and for mixing, and to accelerate chemical processes. Ultrasonics relates to application of ultrasound. Ultrasound can be used for medical imaging, detection, measurement and cleaning. At higher power levels, ultrasonics may be useful for changing the chemical properties of substances.

Ultrasound devices are typically hand-held, or fixed into position, and built for intermittent use and are large, or are not stable, and may require cabling for power- and signal transport, in view of high voltages needed, and are not practical in use, especially for assisting actions under guidance of ultrasound. For guidance during the insertion of a needle into a body part neither of the above are suitable to support the complete procedure.

In principle ultrasound could be used to monitor and determine an amount of fluid being present in a human body. One of the implications is that current ultrasound devices are used intermittently and the patient often cannot move during a monitor procedure, and therefore require very well defined situations.

Some documents refer to ultrasound uses. For instance US 2007/016030 A1 recites an apparatus for cannulation of blood vessels. The apparatus comprises a sensor assembly including two linear transducer arrays oriented perpendicular to each other to form a "T" shape to provide ultrasound images of at least one blood vessel in a portion of a patient's body in two perpendicular planes. The sensor assembly includes a housing having a graphically marked surface to facilitate orientation of the sensor assembly on the patient and guidance of a needle towards a desired target vessel during the cannulation procedure. The housing is configured to engage a frame element having a pair of wings extending laterally therefrom. The apparatus is relatively difficult. U.S. Pat. No. 5,167,630 A recites a cannulation device which is adapted for facilitating the location and venipuncture of a blood vessel with ease and precision. A carrier assembly supports a movable cubic block unit which contains an aligned combination of an ultrasonic probe and a cannula guide path means. The cubic block unit moves laterally within a defined space, whereby a blood vessel is located ultrasonically by blood flow detection, and the guide path means assists venipuncture by a cannula. EP 2 666 414 A1 recites a an ultrasound device, in particular an ultrasound device that is designed for vascular imaging, especially for guiding vascular puncture. WO 2010/111525 A2 recites an apparatus and method for identifying the flexor retinaculum of the carpal tunnel, injecting an effective amount of an agent into at least a portion of flexor retinaculum or tissue adjacent thereto, wherein the agent is configured to weaken the flexor retinaculum. US 2013/131501 A1 recites a neurovasculature access system and device for placing a cannula adjacent to a nerve. EP 2 078 495 A1 recites a device with a main support comprising a horizontal part adapted to a member i.e. lower limb, of a patient and a vertical part forming an angle with respect to the part to move away from the member. A maintaining unit i.e. belt, maintains the support at the member. A ultrasound echographic probe is fixed on a probe support. The probe support is fixed on the part of the main support in a manner to direct the probe towards a region of a body to be explored and in a manner that the part and the maintaining unit are staggered relative to the region.

Therefore there still is a need for an improved ultrasound device, which overcomes one or more of the above disadvantages, without jeopardizing functionality and advantages.

SUMMARY OF THE INVENTION

The present invention relates in a first aspect to a device according to claim 1, also referred to as "vascoscope". The present vascoscope is especially suited for use in dialysis and in central venous cannulation and is aimed to improve first-time successful cannulations and minimize cannulation-associated complications such as infiltration and hematoma formation, which may occur in particular in repetitive use applications. The device comprises a probe for ultrasound imaging. The probe comprises at least one array of n*m ultrasound electro-acoustical elements 11, such as a transducer, for forming an ultra-sound depth image. The array is typically located parallel to a longitudinal axis and centrally located. The image is typically made from a part of a human tissue or tissues, and likewise from a shunt or vein, wherein "vein" is also meant to refer to "artery". The image is to support entry of a needle centrally in a vein or shunt. The probe is provided in a holder, the probe holder adapted to provide rotation of the probe over at least ±45°, preferably over at least ±90°, and typically full rotation of the probe over 360°; i.e. there are no objects or part of objects preventing full rotation. For rotation a pivot 25 may be provided, such as a pivot comprised in the holder or in the probe 25, the pivot configured to provide a matching connection between probe and holder, and providing removability of the probe from the holder, and an opening adapted to the pivot, such as an opening comprised in the probe. The pivot may also be provided as a movable pivot, configured to allow adaptation of a position of the probe relative to the holder. The pivot is typically provided parallel to a rotation axis, such as on a longitudinal axis of the probe and centrally located on said axis. A bottom of the holder 22 is higher than a bottom 12 of the probe, such as at least 0.1 mm higher, such as at least 0.5 mm higher, such that the probe touches the skin continuously, can rotate freely and if required a gel or the like can be applied for supporting image formation. The holder is placed on the skin with more or less pressure, adapting to different skin types and (arm) sizes, in order to allow the probe to touch the skin with the right and relatively light pressure for imaging while still not compressing the underlying shunt. A size of the holder at a front side 24 is typically less than 1 cm more than a size of the probe, even more preferably smaller than the size of the probe (see figures), such that space is left free for imaging and entering the needle. It is noted that the needle is entered relatively close to the probe. Typically the probe can be removably attached to the probe holder, e.g. such that it can be cleaned. In order to support persons entering the needle the present device is fixed by a fixator, such as a strap which can be attached to the holder and can be wrapped around an arm or leg, typically a single strap (in two sections). By fixing the present device with the fixator, yet allowing some movement thereof e.g. in order to correct for small positioning deviations, a person entering a needle has two hands free thereto. Movement of at least 1 mm in at least one direction parallel to a bottom probe plane is possible, preferably movement in any direction parallel to the bottom probe plane. Said person can, when entering the needle, use the display with the image of the probe in order to see the exact position of the needle, e.g. relative to a vein or shunt, while bringing the needle in position. Typically one hand may be used to hold a vein or shunt between two fingers (e.g. thumb and index finger) and the other to enter the needle. The holder, probe, and fixator are configured to leave a space directly adjacent to the front side 24 of the holder free for the fingers to manipulate the shunt and for entry of the needle, such as a space of larger than 1 cm in a direction perpendicular to the front side 24, typically larger than 3 cm, and larger than 3 cm parallel to a tangential of the front side 24, typically larger than 5 cm. FIG. 2f shows a symmetrical layout, wherein also at a back side of the probe a similar space as at the front side are left free. The present device can equally well be operated by left-handers and righthanders. Further a controller, the controller being capable of addressing the electro-acoustical elements and receiving signals from the electro-acoustical elements, the controller in use providing input to the display, and an input for an electrical power source for providing power to at least one of the echoscope, controller and display, are present. By using said device allowing full ultrasound guiding for entering a needle it has been found that miss-pricking is reduced from 20-60% to less than 10%, and for experienced caretakers to less than 5%. Such is a big advantage as e.g. hematomas, puncture of shunts, and so on, as well as discomfort for patients, are prevented, and the lifetime of shunts is increased. The present device is so user-friendly that it can be used by patients themselves by using (for all steps consecutively) only one hand, such as dialysis patients. As a result these patients can use the present device at home, such as for preparation and use of small dialysis equipment in addition.

In a second aspect the present invention relates to a kit of parts comprising a device according to the invention or part thereof, and a box for storing said device.

In a third aspect the present invention relates to a method of echo-guided entering a needle, such as pricking a vein or shunt, comprising providing the present device, forming an ultrasound image with the probe, if relevant detecting a vein or shunt, fixing the device, optionally fixing the vein or shunt with a first hand, entering the needle, such as in the vein or shunt, under guidance of the ultrasound image, and adjusting (lowering) the angle of the needle and entering the needle further, such as into the vein or shunt. The method may be non-medical.

Thereby the present invention provides a solution to one or more of the above mentioned problems and/or disadvantages mentioned throughout the description.

Advantages of the present description are detailed throughout the description.

DETAILED DESCRIPTION OF THE INVENTION

The present invention relates in a first aspect to a device according to claim 1. The device comprises a probe for ultrasound imaging. The probe may comprise a slit 16, and the probe holder may comprise a probe receiver 26, the slit configures to provide rotation and typically oriented parallel to a bottom plane of the probe.

In an exemplary embodiment of the present device a space is left free at a front side of the device as well as at a back side of the device. Therewith the probe can after rotation form an image at either (front and back) side of the holder. A caretaker can then select an appropriate position to enter the needle, which may be at either side.

In an exemplary embodiment of the present device the holder has a symmetry axis.

In an exemplary embodiment of the present device at least one array of electro-acoustical elements 11 may be adapted to form an ultrasound image under an angle of 40-90° relative to the bottom plane of the probe. Therewith the probe can form an ultrasound image of tissue directly in front of the probe or probe holder.

In an exemplary embodiment of the present device the fixator may be rotatably attached to the holder, with a rotation axis preferably substantially parallel to the bottom probe plane, such as by a hinge 32. Therewith the present device is suited for any thickness of body extremity, and at the same time pressure is still distributed properly over the extremity's skin. The hinge is therefore preferably located within 1 cm from a bottom side of the probe holder, such as substantially parallel to the bottom of the holder.

In an exemplary embodiment of the present device the fixator 30 comprises at least one distance piece 31, the distance piece in combination with the rotation configured for maintaining a distance of 1-5 mm of the fixator from an object to be imaged, preferably at least one distance piece at either side of the probe holder, such as a rubber strip, or a ball bearing wherein balls extend partly outwards from the bearing. As such the pressure is well distributed, and rotation of the probe is supported.

In an exemplary embodiment of the present device the display 40 may be integrated in the probe, or wherein the display may be in a wireless connected device, such as a smart phone, or wherein the display may be in (at least one) video glasses 41, wherein the video glasses cover an eye image field for less than 50%, allowing at least one eye to obtain images from above and below the image in the glasses, or may be in an augmented reality glasses, or may be a combination thereof. It is preferred to use glasses, such as video glasses, or augmented reality glasses, as (eye) contact with a patient is maintained, an ultrasound image can be viewed, and the skin of the patient can be viewed, at the same time. The video or augmented reality glasses may include support holders to compensate for varying dimension of corrective glasses already worn by a caretaker.

In an exemplary embodiment of the present device the fixator and in particular the bridge may be made of a resilient material, such as a thermoset or thermoplast polymer, wood, a metal, such as steel, and a lightweight metal, such as aluminium.

In an exemplary embodiment the present device may comprise a fixator with a resilient bridge 38, two legs 33 attached to either sides of the bridge, each leg comprising a clamp section 34, wherein the holder 20 comprises an elastic material, and wherein the holder 20 is attached by a holder attachment 29 to the fixator. The legs may be curved at a lower side thereof, largely following a shape of a human arm (or likewise leg) to which the present device may be attached. The bridge is above the holder and preferably a few mm above the holder. The holder attachment is typically located below the middle of the fixator and preferably at a lower end of the fixator, such as 1-10 mm from the lower end. Above the bridge clamp sections are provided, to be activated by a thumb and finger. The clamp section may comprise a relatively small indentation following a form of a respective finger and thumb. The fixator is typically formed as one part, such as by a mold.

In an exemplary embodiment the present device the holder may comprise an elastic material, such as a natural or chemical rubber, or silicone, preferably with a Youngs modulus of $10^{-3}$-$5*10^{-1}$ GPa (ISO 37), such as $10^{-2}$-$*10^{-1}$ GPa. In rest on the arm the elastic material is typically slightly stretched, and held by its attachments 29, as the length of the holder is somewhat shorter than the equivalent inner circumference length of the fixator. The holder therewith "automatically" adapts to a shape of an arm and fixes the device to the arm. A bridge part of the fixator is typically left free from an underlying arm (or leg). Also the legs of the fixator in use typically may only touch the arm at their lower ends (near 29) arm.

In an exemplary embodiment the present device a leg (38) may comprise a fixator foot (39). The foot may prevent injuries.

In an exemplary embodiment of the present device the fixator 30 may comprise two side portions 36, preferably connected to the holder by an adjustment element 37, such as a flat extension spring 37, such as from the same flexible material, the side portions each individually comprising at least one high density material, the side portions being made of a flexible material, and optionally wherein the side portions form a flat O-ring, such as wherein dimensions of an outer circle of said ring are 10-50 cm, and dimensions of an inner circle are 5-40 cm. For some veins it is difficult to attach a strap or the like, as it is difficult if not impossible to attach the strap, such as around a thorax, and therefore this alternative fixator may be used. An adjustment element, such as flat extension spring, excentre, or screw, may be used to accommodate for small position adjustment of the probe or probe holder. High density material, typically of >2 gr/cm$^3$, preferably of >4 gr/cm$^3$, such as >7 gr/cm$^3$ may be used for firmly fixating.

In an exemplary embodiment of the present device side portions of the fixator may comprise a high friction material, preferably a high friction perpendicular to a virtual axis running from a side portion via the probe holder to the other side portion. Therewith movement of the fixator is limited.

In an exemplary embodiment of the present device the fixator may comprise a central portion (35) comprising a low friction material. Therewith movement of the central portion is supported, e.g. in view of locating a vein.

In an exemplary embodiment of the present device the high density material may comprise a metal or a polymer, preferably selected from lead.

In an exemplary embodiment of the present device the controller may be connected to the probe by a wire 81, preferably a wire attached at a backside of the probe under an angle of 0-60 degrees relative to the bottom plane of the probe, such as under an angle of 20-45 degrees, or is wireless connected, or is integrated in the probe.

In an exemplary embodiment of the present device the probe may be connected to the display by a wire 81, preferably a wire attached at a backside of the probe under an angle of 0-60 degrees relative to the bottom plane of the probe, such as under an angle of 20-45 degrees, or is wireless connected. It is found important, in terms of use, that the wire is attached to a back side and under a low angle (relative to a bottom of the holder/probe), such that scanning is not hindered, the probe/probe holder are stable, the probe can be repositioned with one hand, and no extra forces are exerted on the probe when scanning.

In an exemplary embodiment of the present device the probe may have a width of 0.5-10 cm, such as 1-5 cm, a length of 0.5-10 cm, such as 1-8 cm, a height of 0.1-10 cm, such as 1-5 cm, wherein the probe holder has a height, width and length adapted to the probe, wherein a distance piece may have a height of 0.2-2 cm, such as 0.5-1 cm, and a length of 0.5-5 cm, such as 1-4 cm.

In an exemplary embodiment of the present device the device is transportable.

In an exemplary embodiment of the present device the probe holder and/or probe may comprise an indentation 27 in a central portion thereof, wherein the indentation is preferably in the form of a circle section, or ellipse section, or in the form of a V, preferably wherein the indentation is provided over 30-50% of a surface area of the probe holder at a front side thereof, therewith allowing a portion of underlying material (skin) to remain visible.

In an exemplary embodiment of the present device the probe holder and/or probe may comprise needle guider 28, such as one or two extensions (1-5 mm), a light source, such as a laser or LED, configured to form an optical indication visible on a skin, such as a line or a spot. Typically the needle guider points towards a location about 5-8 mm ahead of the probe.

In an exemplary embodiment of the present device the controller may be located in the probe or in a housing or in the display.

In an exemplary embodiment of the present device the probe may form 3D images.

In an exemplary embodiment of the present device the probe 10 may have a circular, rectangular, multigonal, ellipsoidal cross-section, or a combination thereof, preferably a rectangular or multigonal cross-section.

In an exemplary embodiment of the present device the probe 10 and/or holder 20 may have at least one oblique side.

In an exemplary embodiment of the present device the probe 10 may comprise a receiving element 15 for a display, preferably a lightweight display, such as a sphere, or wherein the display is integrated in the probe.

In an exemplary embodiment of the present device the probe 10 may comprise at least one of a metal shield 13 at a top side of the probe, a backing material 14, an acoustic absorber 17, a piezo electric element 18 at a bottom side of the probe, and there below an acoustic lens 19.

In an exemplary embodiment of the present device the receiving element (15) may be spaced apart from the probe, such as at a distance of 1-3 cm.

In an exemplary embodiment of the present device in the array of electro-acoustical elements 11 may comprise n*m electro-acoustical elements, wherein n∈[1,10] and m∈[2, 210], and optionally at least one second array of electro-acoustical elements located under an angle of 45-90° with respect to the at least one first array of electro-acoustical elements, such as in the form of a (combined) T or X.

In an exemplary embodiment of the present device at least one first electro-acoustical element, such as a bulk piezo-electric crystal or a microelectromechanical system (MEMS), may be capable of generating an ultrasound frequency pulse of 20 kHz-50 MHz, and wherein at least one second electrical acoustical element may be capable of detecting a reflected ultrasound frequency pulse such as of a few milliseconds to microseconds duration of 20 kHz-50 MHz.

In an exemplary embodiment the present device may comprise a voltage controller for applying a voltage to the electro-acoustical element. In view of higher voltages being applicable, a controller is found to improve the quality of images formed and received.

In an exemplary embodiment the present device may comprise at least one array of first electro-acoustical elements, and/or may comprise at least one array of second electro-acoustical elements. Therewith frequencies, responses, images, and so may be varied.

In an exemplary embodiment of the present device the electro-acoustical elements may be capable of operating separately, sequentially, in phase-shift mode, in parallel mode, in frequency scan mode, in spatial scan mode, in intensity mode, in pulsed mode, variations thereof, and combinations thereof, preferably providing a multi-frequency spectrum of ultrasounds and/or powers.

In an exemplary embodiment of the present device at least one first electro-acoustical element may have a centre frequency of 20 kHz-50 MHz, preferably 50 kHz-10 MHz, such as 10 kHz-3 MHz, an active area of $4*10^{-4}$-2000 mm$^2$, preferably $10^{-3}$-500 mm$^2$, more preferably $10^{-2}$-100 mm$^2$, even more preferably $10^{-1}$-50 mm$^2$, such as 1-20 mm$^2$, and a near field length of 0.1-50 mm, preferably 0.2-30 mm, such as 1-20 mm. Therewith ultrasound images can be further optimized and adapted to given boundary situation, such as tissue being imaged.

In an exemplary embodiment of the present device at least one electro-acoustical element may comprise at least one MEMS, the MEMS comprising at least one piezo-electric element, a cavity, and one or more of an ultrasound absorbing layer, quarter lambda reflecting (multi)layer, and an ultrasound reflecting layer, wherein the MEMS comprises a stack of layers, the stack comprising (i) at least two piezo-electric elements poled in a same direction, each piezoelectric element comprising a top electrode layer, a piezoelectric layer, and a bottom electrode layer, wherein the top electrode covers the piezoelectric layer completely or partially, and wherein the piezoelectric layer covers the bottom electrode completely or partially, and preferably a voltage splitter, for applying a voltage to an individual piezoelectric element.

In an exemplary embodiment of the present device the at least one cavity comprises an ultrasound absorbing material, and the voltage source and the at least one electro-acoustical element are in direct contact In an exemplary embodiment of the present device the stack of the MEMS may comprise (i) at least two piezoelectric elements poled in a same direction, each piezoelectric element comprising a top electrode layer, a piezoelectric layer, and a bottom electrode layer, wherein the top electrode covers the piezoelectric layer completely or partially, and wherein the piezoelectric layer covers the bot-tom electrode completely or partially, wherein preferably at least one of a length of the MEMS is 10-2500 µm, preferably 15-1000 µm, more preferably 25-500 µm, such as 50-200 µm, a width of the MEMS is 5-1000 µm, preferably 10-250 µm, more preferably 20-100 µm, a thickness of the piezoelectric layer is 0.1-10 µm, preferably 0.25-5 µm, more preferably 0.5-2.5 µm, the electrode layer is selected from metals, and metallic conductors, a thickness of the electrode layer is 0.1-10 µm, preferably 0.25-5 µm, more preferably 0.5-2.5 µm, the piezoelectric layer is selected from PZT, AlN, PMNT, and combinations thereof, the dielectric layer is selected from $SiO_2$, and $Si_4N_3$, a thickness of the dielectric layer is 0.1-10 µm, preferably 0.25-5 µm, more preferably 0.5-2.5 µm, the bottom layer is selected from $SiO_2$, Si, SiC, and $Si_4N_3$, a thickness of the bottom layer is 1-500 µm, preferably 2.5-250 µm, more preferably 5-100 µm, an adhesive layer is present between an electrode layer and a piezoelectric layer, comprising a cavity, and at least one of an ultrasound absorbing (multi)layer, quarter lambda reflecting (multi)layer, and ultrasound reflecting (multi)layer, comprising $2\text{-}2^{20}$ piezoelectric elements, preferably $3\text{-}2^{10}$ piezoelectric elements, more preferably $4\text{-}2^5$ piezoelectric elements, wherein high end applications, such as for 3D-imaging, may have a large number of piezoelectric elements, such as $2^{14}$, the piezoelectric layer is a laser assisted sputtering layer, wherein the piezoelectric layer comprises crystalline granular elements, and at least one piezoelectric layer has an intrinsic electrical polarity. In an example the present device may comprise at least one apodization filter. The filter may correct for signals provided by the present system and reflections obtained. In an example of the present portable device the cavity may comprise an ultrasound absorbing material, such as epoxy. Therewith unwanted ultrasound signal are substantially blocked.

In an exemplary embodiment the present device may comprise a transceiver (c) for communication, such as wireless communication, between the device and an external supporting device. Therewith images can be directly stored on a further device, can be viewed on a connected further device, etc.

In an exemplary embodiment the present device may comprise stored on the device and/or stored on the external supporting device software and/or gathered data.

In an exemplary embodiment of the present method the method may be performed at a home of a patient single-handed by the patient. The one available hand is used, in sequence, to execute the steps of identifying a location of a shunt, forming an ultrasound image with the probe, detecting a vein or shunt, pricking a needle in the vein or shunt under guidance of the ultrasound image with a first hand, and adjusting the angle of the needle and entering the needle further into the vein or shunt.

In an exemplary embodiment the present method may comprise fixing the device, and fixing the vein or shunt, such as with a second hand. It is noted that a second hand is not needed, and that it is preferred not to use a second hand and to rely completely on ultrasound imaging, which apparently seems to be a matter of getting accustomed to the present system.

In an exemplary embodiment of the present method blood from the vein is dialyzed.

The invention is further detailed by the accompanying figures and examples, which are exemplary and explanatory of nature and are not limiting the scope of the invention.

SUMMARY OF FIGURES

FIGS. 9a-d show an alternative embodiment of the present fixator and holder.

DETAILED DESCRIPTION OF FIGURES

Figure 1A:
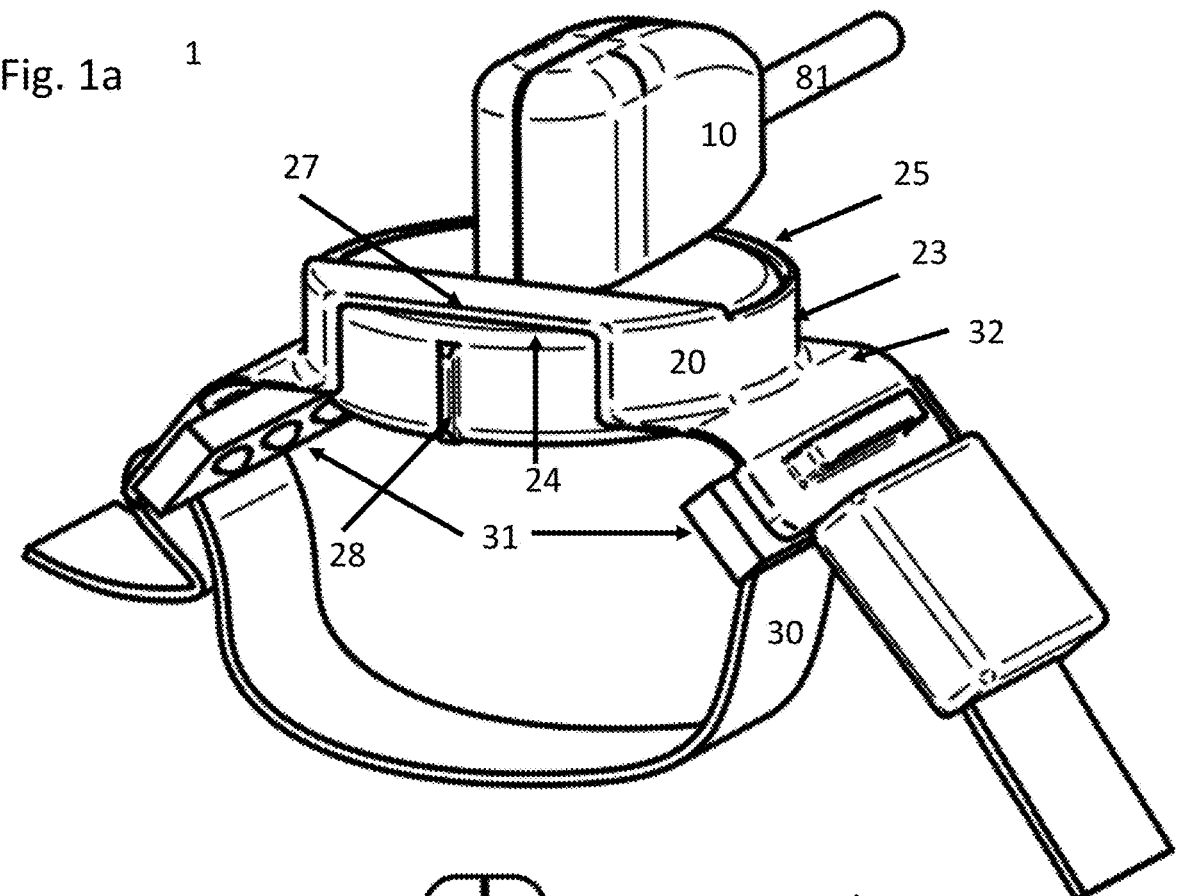
FIGS. 1a-d and 2a-f show schematical layouts of the present vascoscope.

In the figures:
1 device
10 probe
11 array of transducers
12 bottom of probe
13 metal shield
14 damping material
15 display receiving element
16 slit
17 acoustic absorber
18 piezo electric element
19 acoustic lens
20 probe holder
22 bottom of holder
23 side of holder
24 front side of holder (may be void)
25 pivot (axis)
26 probe receiver
27 indentation
28 optical needle guider
29 holder attachment
30 fixator
31 distance piece
32 hinge
33 fixator leg
34 fixator clamp
35 central portion fixator
36 side portion fixator
37 adjustment element
38 fixator bridge
39 fixator foot
40 display
41 video glasses
71 top/bottom electrode layer
72 piezoelectric layer
73 stiff layer
74 dielectric layer
81 wire
91 video glasses
92 computer
93 software
94 beamformer
95 exemplary probe
96 exemplary fixator FIG. 1a shows the present probe 10, with a wire 81, a probe holder 20, an indentation 27 at a front end, a needle guider in the form of a light source (LED) and a slit providing a visual line on a skin, a side 23 of the holder, a void front side of the holder, a hinge 32, a fixator 30 (strap), and distance piece 31 in the form of ball bearings.

Figure 1B:
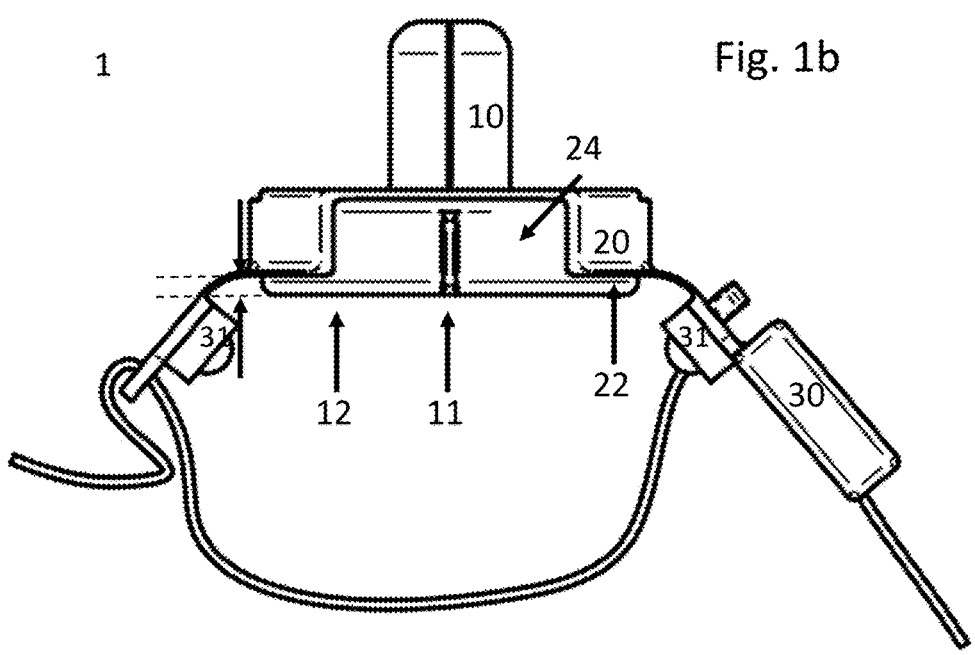

FIG. 1b shows a side view of FIG. 1a, with further an array of transducers 11, a bottom of the probe 12 located lower than a bottom 22 of the probe holder (indicated with arrows).

Figure 1C:
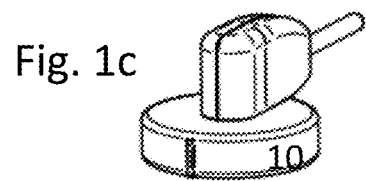
Figure 1D:
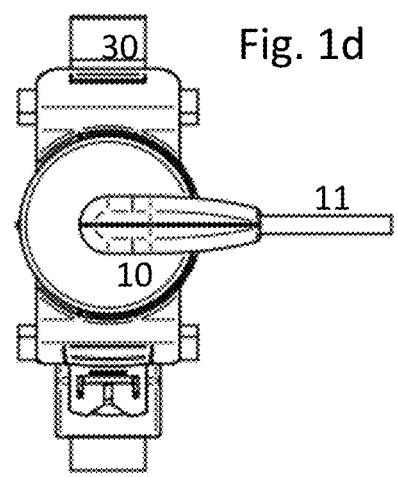

FIG. 1c shows the device taken apart into the various elements thereof, and FIG. 1d shows a top view.

FIGS. 2a-f show alternative embodiments.

Figure 2A:
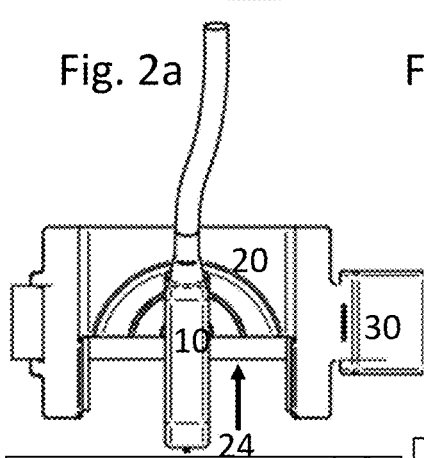

FIG. 2a shows a probe 10, a probe holder 20, a fixator 30, and a front side 24 of the probe holder that is void, leaving space for image forming and entering a needle.

Figures 2B, 2C:
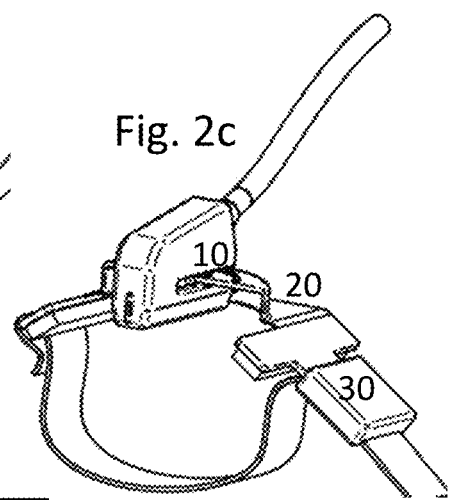

FIG. 2b shows a side view and FIG. 2c an aerial view.

Figure 2D:
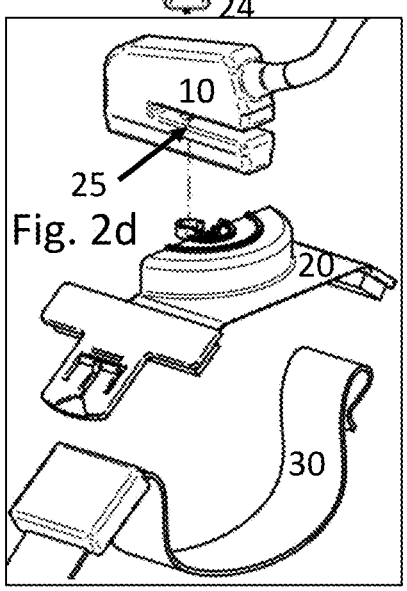

FIG. 2d shows the device taken apart, with the probe 10, probe holder 20, and fixator 30, and further a pivot 25 for rotating the probe in the holder, the holder comprising a pivot receiving element.

Figure 2E:
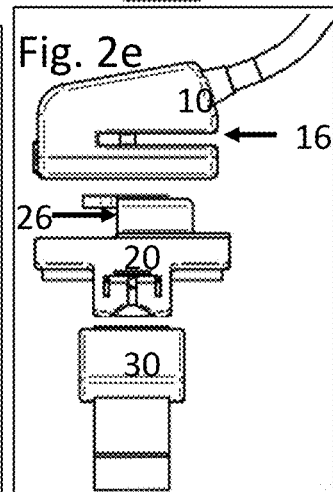

FIG. 2e shows a slit 16 for removably attaching the probe to holder 20, with a slit receiving element 26 in the holder.

Figure 2F:
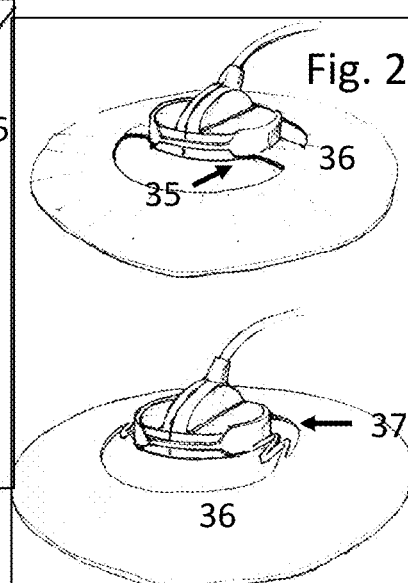

FIG. 2f shows an alternative fixator which comprises a side portion 36, and may comprise a central portion 35, and a flat extension spring 37.

Figure 3A:
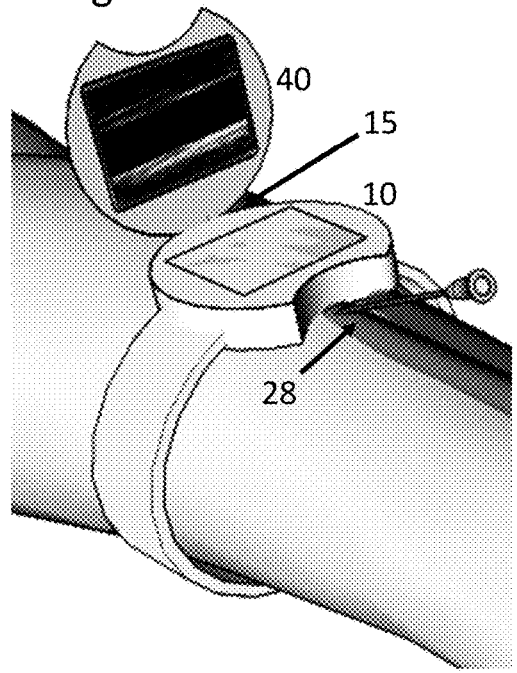
FIGS. 3a-c show a use of the present vascoscope.

FIG. 3a shows an overview of the present device attached to an arm, with a probe 10 and display 40. A needle is entered.

Figure 3B:
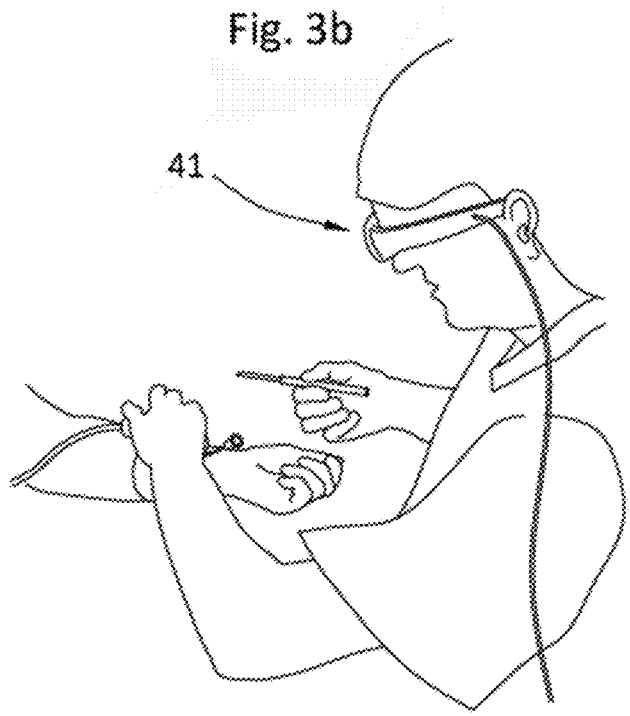

FIG. 3b shows a caretaker using the present device with video glasses (or likewise AR glasses) 42, taking a vein between thumb and index finger of the left hand and entering a needle with the right hand.

Figure 3C:
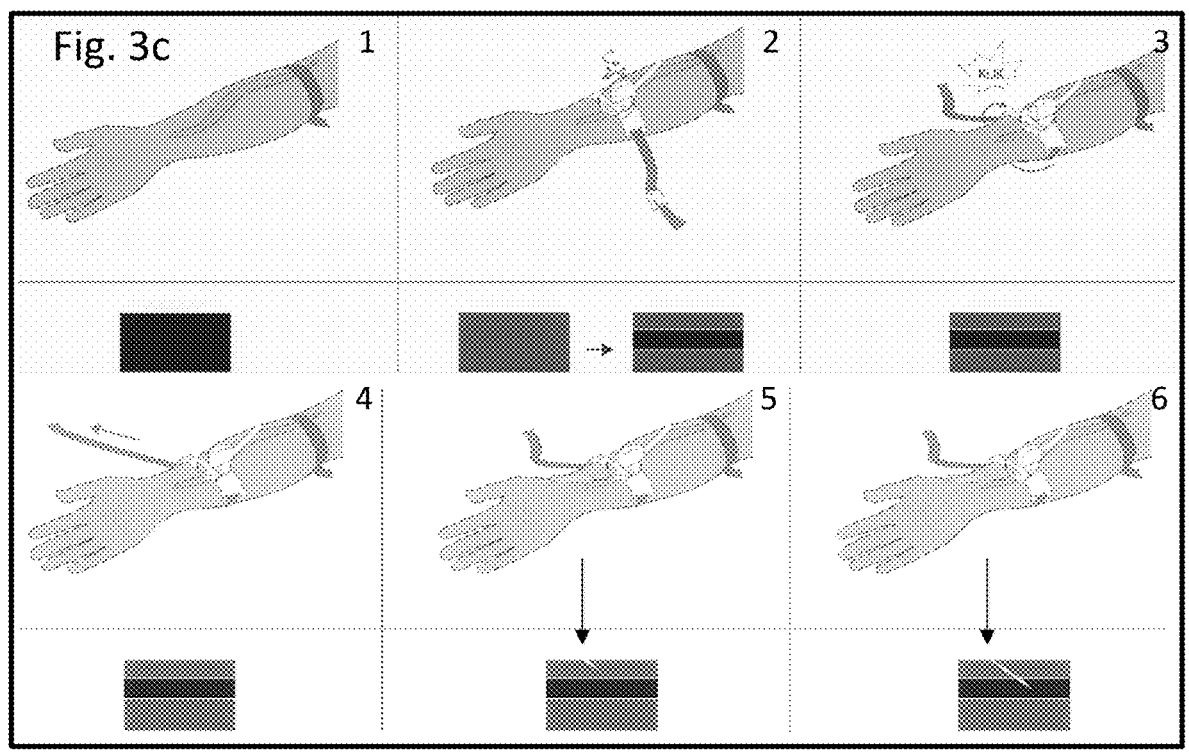

FIG. 3c schematically shows the process of (1) using a pressure wrap to make a vein visible, (2) using the present device to identify a location of a vein (dark coloured part in bottom part of the figure), (3) fixing the device to the arm for holding the device in position, (4) tightening the fixator, (5) entering a needle (indicated with an arrow) under ultrasound image guidance, and (6) entering the needle (indicated with an arrow) under ultrasound image guidance in the vein.

Figure 4A:
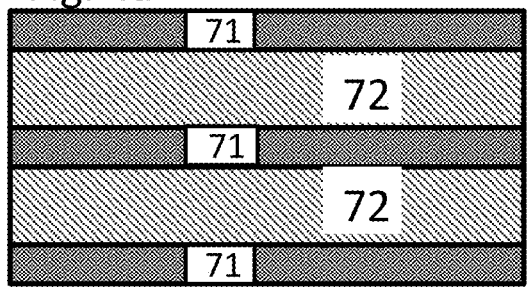
FIGS. 4a-d show layouts of the present MEMS.

In FIG. 4a a basic piezoelectric element is shown. Therein, from top to bottom, a top electrode layer 71, a piezoelectric layer 72, a bottom electrode 71, also functioning as a top electrode layer 71, a piezoelectric layer 72, and a bottom electrode 71 are shown. To the top electrode a first voltage may be applied, to the middle electrode a second potential, and to the bottom electrode a third potential, such as +50 V, 0 V, −50 V, and 100 V, 50 V and 0V, respectively. A voltage may be provided as such, or as a split voltage from one source.

Figure 4B:
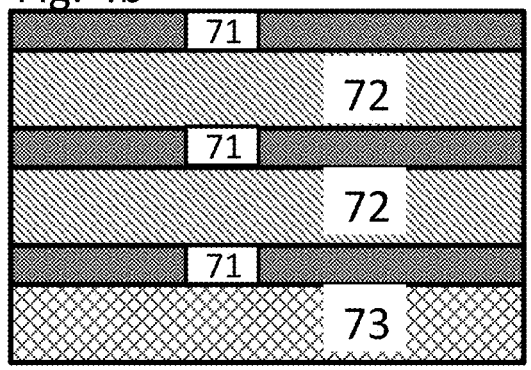

In FIG. 4b, in addition to FIG. 1a, a stiff layer 73 is present, such as a SiN layer. The layer may be at the bottom, it may be at the top, and both. Further a stiff layer may be present in between the bottom electrode 71 of the top piezoelectric layer, and the top electrode 71 of the bottom electrode layer, in which case the bottom and top electrode are not the same.

Figure 4C:
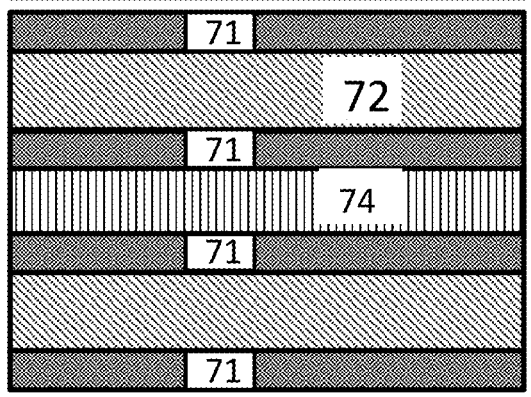

In FIG. 4c, compared to FIG. 1a, a dielectric layer 74 in between the bottom electrode 71 of the top piezoelectric layer, and the top electrode 71 of the bottom electrode layer, is present.

Figure 4D:
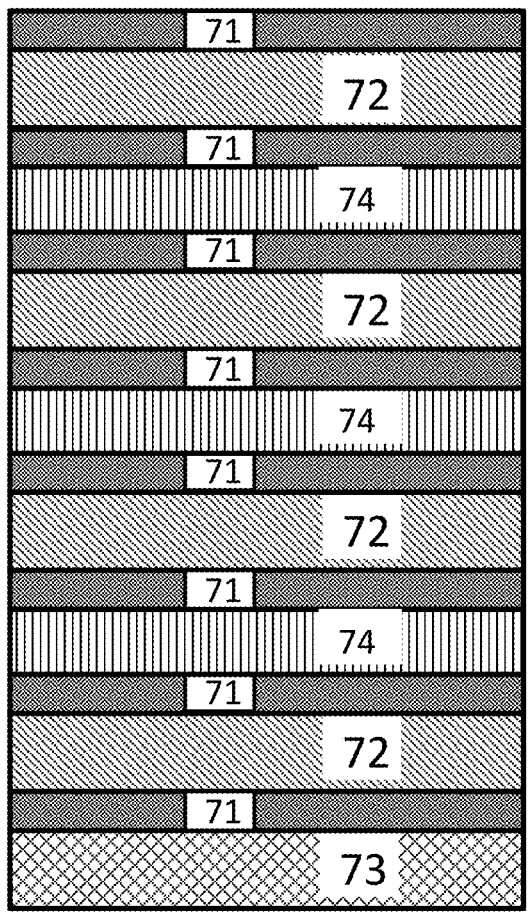

In FIG. 4d four piezoelectric elements, each comprising a top electrode layer 71, a piezoelectric layer 72, and a bottom electrode layer 71, with in between a dielectric layer 74, and a stiff layer 73 is present. Each piezo-electric layer may have a voltage of e.g. 50 V, which may be a split voltage from one single source. A total voltage over the layers would then be 200 V.

Figure 5:
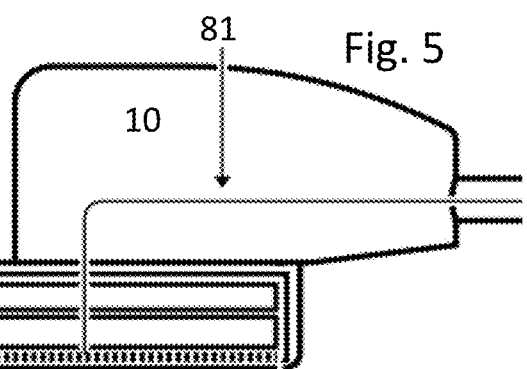
FIG. 5 shows a layout of the probe.

FIG. 5 shows a schematic layout of the present probe 10. Therein a coaxial wire 81, a metal shield 13 essentially surrounding a bottom part and leaving the bottom open, an acoustic lens 19, such as an array of holes or a path-length refractor, a piezo electric element 18, acoustic absorber 17, typically a layer, such as a foam layer, such as a urethane layer, and a damping material 14, such as a layer, e.g. a layer of tungsten loaded epoxy, such as araldite, are shown. Typically also a ground electrode is present.

Figure 6:
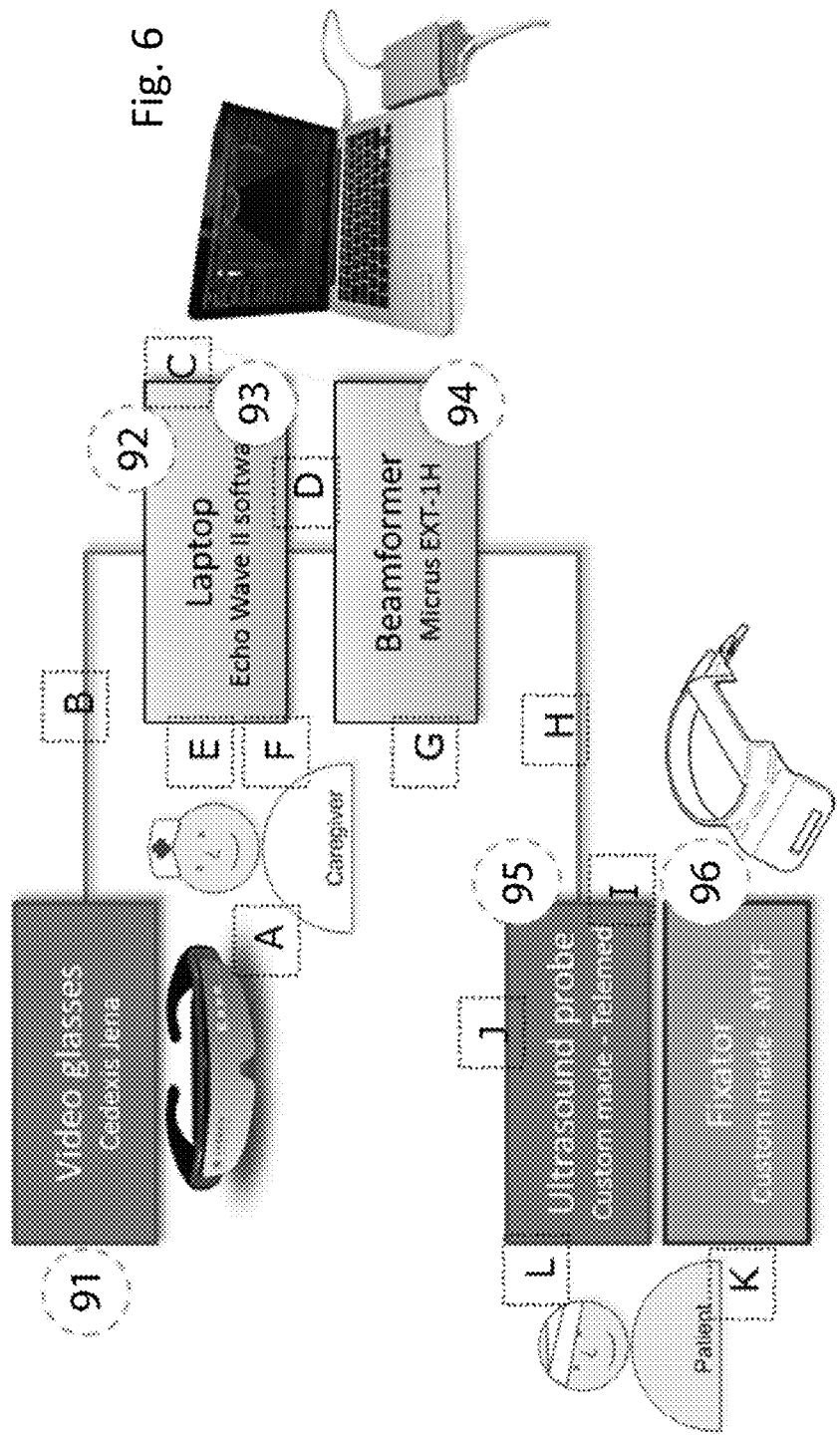
FIGS. 6-8 show further details of the invention.

In FIG. 6 schematics of operation are shown. Cedexis Jena video glasses are in connection with a computer. On the computer software for addressing transducers, processing ultrasound signals, forming ultrasound images, communication between various elements of the present device, and so on, is stored. The ultrasound images are formed with a MicrUs EXT-1H™ beamformer (shown to the right of the computer). The beamformer is incorporated in the present ultrasound probe, which is custom made by Telemed. Also the fixator is custom made by MTKF. Connections are indicated with capital letters A-K, and elements are indicated with numbers 91-96.

Figure 7:
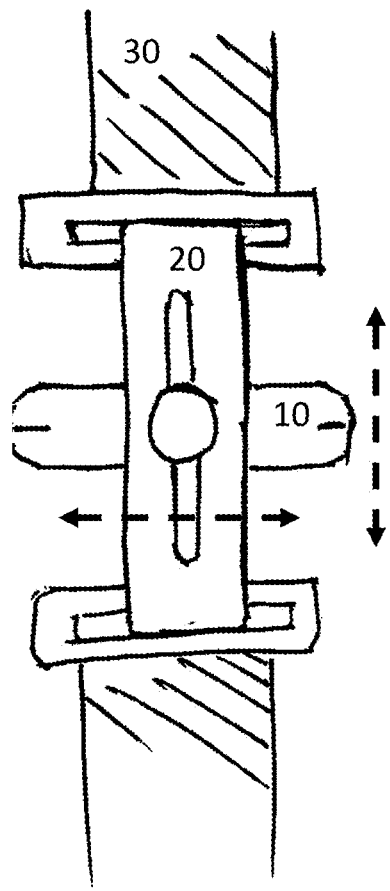

FIG. 7 shows an exemplary embodiment wherein the probe 10 can move relative to the holder 20. The fixator 30 can be attached to a patient at one specific location and still providing movement of the probe in two directions.

Figure 8:
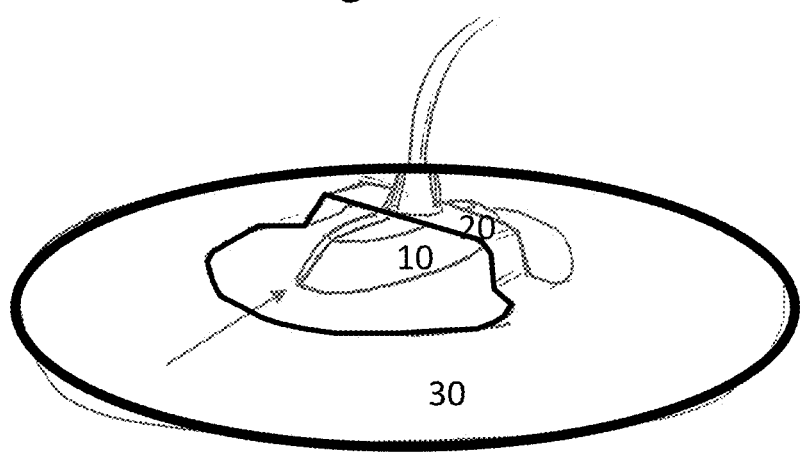

FIG. 8 shows an elliptical, symmetrical, oblique probe.

An elliptical shaped probe provides both stability of and available space of a narrow variant. The symmetrical shaped probe and holder provide that both the front and the back can be pricked. Very practical when the shunt must be punctured from 2 sides, the whole system does not have to be removed and turned over. A sloping edge of the probe (narrow from the top, wide from the bottom) is also provided. So that the nurse, even when looking at the probe, can see exactly where the line on the front is exactly on the skin. This means that the caretaker knows exactly where the transducer is located and where it needs to be pinned.

FIGS. 9a-d show an alternative embodiment of the present fixator and holder. In FIG. 9a the elastic holder 20, fixator 30 with bridge 38, legs 33, clamps 34, and feet 39 are shown. The holder is at a lower part of the fixator attached to the fixator by attachment 29. FIG. 9b shows opening of the present fixator by a thumb and finger action. The device can then be positioned on e.g. a human arm. In FIG. 9c the present probe can be rotated and slid and if required the device can be repositioned, such as up or down the arm, or towards a side of the arm, or both. In FIG. 9d a needle is entered into a vein using the present device.

Further details of the figures are given throughout the description.

EXAMPLES

Measurement Procedure

With reference to FIG. 3c. 1: The shunt and skin are inspected. Then a tourniquet is applied. As a preparation ultrasound gel is applied to the probe. And for imaging video glasses are placed on the caretaker's head. 2: The probe with holder is placed on the arm. Then the shunt-traject is inspected using the ultrasound image formed by the probe. The best place for first shunt access is then selected. 3,4: The probe is fixed to the arm and on the specified place by connecting the tourniquet-system band and pulling the band slightly. This enables proper fixation and prevents indentation of the shunt. 5,6: The needle is pushed through the skin and underlying tissue into the shunt, guided by the ultrasound image. Next a blood line is connected. Finally the probe and holder are disconnected and may be moved to a second access location.

The invention although described in detailed explanatory context may be best understood in conjunction with the accompanying examples and figures.

The invention claimed is:

1. A device for assisting entry of a needle comprising
a probe comprising at least one array of n*m ultrasound electro-acoustical elements, wherein in the array of electro-acoustical elements comprises n*m electro-acoustical elements, wherein $n \in [1,10]$ and $m \in [2,2^{10}]$, for forming an ultrasound depth image,
a holder for the probe, the probe holder adapted to provide rotation of the probe over at least ±45°, wherein a bottom of the holder is higher than a bottom of the probe,
a fixator attached to both sides of the holder for maintaining the holder in a spatial position, and also adapted to provide translational repositioning of the holder and probe of at least 1 mm in at least one direction parallel to a bottom probe plane,
wherein the holder and fixator are configured to leave a space directly adjacent to the front side of the probe free for entry of the needle and for tactile control of a vein or shunt,
a display for providing an ultrasound image of the probe,
a controller, the controller being capable of addressing the electro-acoustical elements and receiving signals from the electro-acoustical elements, the controller in use providing input to the display,
an input for an electrical power source for providing power to at least one of the probe, controller and display, and
wherein at least one array of electro-acoustical elements is adapted to form an ultrasound image under an angle of 40-90° relative to the bottom plane of the probe,
wherein the probe can be removably attached to the probe holder,
wherein the fixator is adapted to provide translational repositioning of the holder and probe of at least 1 mm in at least one direction parallel to a bottom probe plane movement in any direction parallel to the bottom probe plane, and
wherein the space is larger than 1 cm in a direction perpendicular to the front side.

2. The device according to claim 1, wherein a size of the holder at a front side is less than 1 cm more than a size of the probe, and wherein the fixator is removably attached to the probe holder, and wherein the space is larger than 1 cm in a direction perpendicular to the front side.

3. The device according to claim 1, wherein the fixator is rotatably attached to the holder, a rotation axis thereof being substantially parallel to the bottom probe plane.

4. The device according to claim 1, wherein the fixator comprises at least one distance piece, the distance piece in combination with the rotation configured for maintaining a distance of 1-5 mm of the fixator from an object to be imaged, and a ball bearing wherein balls extend partly outwards from the bearing.

5. The device according to claim 1, wherein the display is integrated in the probe, or wherein the display is in a wireless connected device, or wherein the display is in a video glasses, wherein the video glasses cover an eye image field for less than 50%, allowing at least one eye to obtain images from above and below the glasses, or is in an augmented reality glasses, or is a combination thereof.

6. The device according to claim 1, wherein the fixator comprises two side portions, the side portions each individually comprising at least one high density material, the side portions being made of a flexible material, and wherein the side portions form an O-ring.

7. The device according to claim 1, wherein the controller is connected to the probe by a wire, or is wireless connected, or is integrated in the probe.

8. The device according to claim 1, wherein the probe is connected to the display by a wire, or is wireless connected.

9. The device according to claim 1, wherein the fixator comprises a resilient bridge, two legs attached to either sides of the bridge, each leg comprising a clamp section, wherein the holder comprises an elastic material, wherein the holder is attached by a holder attachment to the fixator.

10. The device according to claim 1, wherein the device is transportable.

11. The device according to claim 1, wherein the probe holder and probe comprises an indentation in a central portion thereof, therewith allowing a portion of underlying material to remain visible.

12. The device according to claim 1, wherein the probe holder and probe comprises needle guider.

13. The device according to claim 1, wherein the probe forms 3D images.

14. The device according to claim 1, wherein the probe comprises at least one of a receiving element for a display, wherein the display is integrated in the probe, a metal shield, a backing material, an acoustic absorber, a piezo electric element, and an acoustic lens.

15. The device according to claim 1, and at least one second array of electro-acoustical elements located under an angle of 45-90° with respect to the at least one first array of electro-acoustical elements.

16. The device according to claim 1, wherein at least one first electro-acoustical element has a center frequency of 20 kHz-50 MHz, an active image forming area of $4*10^{-4}$-2000 $mm^2$, and a near field length of 0.1-50 mm.

17. The device according to claim 1, wherein at least one electro-acoustical element comprises at least one microelectromechanical system (MEMS), the MEMS comprising at least one piezoelectric element, a cavity, and one or more of an ultrasound absorbing layer, a quarter lambda reflecting (multi)layer, and an ultrasound reflecting layer, wherein the MEMS comprises a stack of layers, the stack comprising
(i) at least two piezoelectric elements poled in a same direction, each piezoelectric element comprising
a top electrode layer,
a piezoelectric layer, and
a bottom electrode layer, wherein the top electrode covers the piezoelectric layer completely or partially, and wherein the piezoelectric layer covers the bottom electrode completely or partially.

18. The device according to claim 1, comprising a transceiver (c) for communication between the device and an external supporting device, and
comprising stored on the device and stored on the external supporting device software and gathered data, and
wherein the holder or the probe comprises a pivot, and wherein the holder comprises a slit receiving element and the probe comprises a slit.

19. A kit of parts, comprising the device according to claim 1, and a box for storing said device.

* * * * *